(12) United States Patent
Leyva et al.

(10) Patent No.: US 9,895,461 B2
(45) Date of Patent: Feb. 20, 2018

(54) DEVICES, SYSTEMS AND METHODS FOR TREATING MEDICAL DEVICES HAVING PASSAGEWAYS WITH OZONE GAS

(71) Applicant: SoClean, Inc., Oxford, MA (US)

(72) Inventors: Timothy Leyva, Bellingham, MA (US); William E. Olszta, Webster, MA (US)

(73) Assignee: SoClean, Inc., Oxford, MA (US)

( * ) Notice: Subject to any disclaimer, the term of this patent is extended or adjusted under 35 U.S.C. 154(b) by 0 days.

(21) Appl. No.: 15/481,919

(22) Filed: Apr. 7, 2017

(65) Prior Publication Data

US 2017/0209610 A1 Jul. 27, 2017

Related U.S. Application Data

(63) Continuation of application No. 15/141,216, filed on Apr. 28, 2016, now Pat. No. 9,669,124, which is a continuation-in-part of application No. PCT/US2015/029418, filed on May 6, 2015, and a continuation-in-part of application No. 14/232,773,
(Continued)

(51) Int. Cl.
*A61L 2/20* (2006.01)

(52) U.S. Cl.
CPC ........... *A61L 2/202* (2013.01); *A61L 2202/11* (2013.01); *A61L 2202/24* (2013.01)

(58) Field of Classification Search
CPC ............... A61L 2/202; A61L 2/20; A61L 2/18
See application file for complete search history.

(56) References Cited

U.S. PATENT DOCUMENTS

| | | | |
|---|---|---|---|
| 4,035,657 A | 7/1977 | Carlson | |
| 4,207,291 A * | 6/1980 | Byrd | B01D 53/8675 422/122 |
| 4,465,522 A | 8/1984 | Taldo et al. | |

(Continued)

FOREIGN PATENT DOCUMENTS

| | | |
|---|---|---|
| CN | 1377708 | 11/2002 |
| CN | 105031693 | 11/2015 |

(Continued)

OTHER PUBLICATIONS

U.S. Office Action dated Aug. 3, 2017, issued in U.S. Appl. No. 15/141,152, 14 pages.
(Continued)

*Primary Examiner* — Donald R Spamer
(74) *Attorney, Agent, or Firm* — Grossman Tucker Perreault & Pfleger PLLC

(57) ABSTRACT

The present disclosure is generally related to devices, methods and systems for cleaning, disinfecting and/or sterilizing a medical device, medical hoses and tubes and accessories thereof with ozone gas, in particular the disclosure relates to devices, methods and systems with multiple receptacles for providing closed-loop fluid pathways to distribute ozone gas to inner passageways and the outer compartments of medical devices. The devices in accordance with an embodiment of the disclosure have two or more receptacles for distributing ozone gas, a gas-tight compartment, an ozone operating system, and one or more connector units configured to fluidly migrate ozone in closed-loop treatment systems.

21 Claims, 6 Drawing Sheets

Related U.S. Application Data filed as application No. PCT/US2012/046593 on Jul. 13, 2012, now Pat. No. 9,358,316.

(60) Provisional application No. 61/508,341, filed on Jul. 15, 2011.

(56) References Cited

U.S. PATENT DOCUMENTS

| | | | |
|---|---|---|---|
| 4,517,159 A | | 5/1985 | Karlson |
| D295,074 S | | 4/1988 | Jerge et al. |
| 4,743,275 A | | 5/1988 | Flanagan |
| 4,787,980 A | | 11/1988 | Ackermann et al. |
| 5,207,237 A | * | 5/1993 | Langford ............... A61L 2/202 134/102.1 |
| 5,344,622 A | * | 9/1994 | Faddis ..................... A61L 2/24 219/396 |
| 5,508,006 A | | 4/1996 | Gabele et al. |
| D371,203 S | | 6/1996 | Deeds |
| D390,645 S | | 2/1998 | Hanrahan et al. |
| 5,761,069 A | | 6/1998 | Weber et al. |
| 6,024,066 A | | 2/2000 | Nakayama et al. |
| 6,276,304 B1 | | 8/2001 | Tai |
| 6,280,633 B1 | | 8/2001 | Conrad et al. |
| 6,379,632 B1 | | 4/2002 | Kinoshita et al. |
| D476,423 S | | 6/2003 | Picot et al. |
| 6,576,190 B1 | | 6/2003 | Park |
| D487,315 S | | 3/2004 | Picot et al. |
| 6,752,151 B2 | | 6/2004 | Hill |
| 7,022,225 B1 | | 4/2006 | Clawson et al. |
| 7,520,910 B2 | | 4/2009 | Tilley |
| 7,527,603 B2 | | 5/2009 | An |
| 7,676,276 B2 | | 3/2010 | Karell |
| 7,767,168 B2 | | 8/2010 | Namespetra et al. |
| 7,794,522 B2 | | 9/2010 | Bliss et al. |
| 7,845,350 B1 | | 12/2010 | Kayyali et al. |
| 8,051,853 B2 | | 11/2011 | Berthon-Jones |
| 8,146,946 B1 | | 4/2012 | Emond |
| 8,176,771 B2 | | 5/2012 | Onishi et al. |
| 8,431,076 B2 | | 4/2013 | Fraundorter |
| D692,155 S | | 10/2013 | Matoba et al. |
| 8,815,164 B1 | | 8/2014 | Al Azemi |
| 8,915,380 B2 | | 12/2014 | Sowerby et al. |
| 9,022,247 B2 | | 5/2015 | Enigmann |
| D733,315 S | | 6/2015 | Lui |
| D733,316 S | | 6/2015 | Lui |
| D748,280 S | | 1/2016 | Lui |
| 9,358,316 B2 | | 6/2016 | Leyva |
| D761,142 S | | 7/2016 | Golta et al. |
| D776,290 S | | 1/2017 | Wan et al. |
| 2003/0000966 A1 | | 1/2003 | Shelton |
| 2003/0063997 A1 | * | 4/2003 | Fryer ..................... A61L 2/208 422/3 |
| 2004/0251125 A1 | | 12/2004 | Yu |
| 2005/0017380 A1 | | 1/2005 | Namespetra et al. |
| 2005/0019237 A1 | | 1/2005 | Riley |
| 2005/0186108 A1 | | 8/2005 | Fields |
| 2005/0220665 A1 | | 10/2005 | Ding |
| 2006/0130834 A1 | | 6/2006 | Chen |
| 2006/0272682 A1 | | 12/2006 | Langford |
| 2007/0031778 A1 | | 2/2007 | Helfenbein et al. |
| 2007/0065335 A1 | | 3/2007 | Bedard et al. |
| 2009/0267242 A1 | | 10/2009 | Nichols et al. |
| 2010/0111792 A1 | | 5/2010 | Nelson |
| 2012/0164025 A1 | | 6/2012 | Stockley, III et al. |
| 2012/0227745 A1 | | 9/2012 | Arcilla et al. |
| 2013/0239994 A1 | | 9/2013 | Przyjemski |
| 2015/0004061 A1 | | 1/2015 | Kain et al. |
| 2017/0202990 A1 | | 7/2017 | Leyva |

FOREIGN PATENT DOCUMENTS

| | | |
|---|---|---|
| JP | 2005270589 | 10/2005 |
| KR | 1020040098412 | 11/2004 |
| WO | 03068274 | 8/2003 |
| WO | 2008116165 | 9/2008 |
| WO | 2011058472 | 5/2011 |
| WO | 2013012696 | 1/2013 |

OTHER PUBLICATIONS

Ozone MSDS (Material Safety Data Sheets), Ozone Solutions, Jun. 1, 2000, http://www.ozoneapplications.com/info/ozone_msds.htm, 5 pages.

CPAP Guardian TB-316, America Tyson Industrial Group (Asia Pacific) Limited, http://www.ecvv.com/products/2314441.html, Nov. 91, 2009, downloaded from Internet Jul. 8, 2016, 3 pages.

International Search Report and Written Opinion dated Sep. 17, 2012, issued in PCT Application No. PCT/US12/46593, 6 pages.

International Search Report and Written Opinion dated Jul. 24, 2015, issued in PCT Application No. PCT/US15/29418, 9 pages.

U.S. Office Action dated Jun. 30, 2016, issued in U.S. Appl. No. 15/141,216, 13 pages.

U.S. Office Action dated Jul. 13, 2016, issued in U.S. Appl. No. 15/142,060, 18 pages.

U.S. Office Action dated Jul. 14, 2016, issued in U.S. Appl. No. 15/142,111, 10 pages.

U.S. Office Action dated Jul. 28, 2016, issued in U.S. Appl. No. 15/142,085, 15 pages.

U.S. Office Action dated Oct. 6, 2016, issued in U.S. Appl. No. 15/141,152, 11 pages.

U.S. Office Action dated Nov. 23, 2016, issued in U.S. Appl. No. 15/141,216, 9 pages.

U.S. Office Action dated Nov. 23, 2016, issued in U.S. Appl. No. 15/142,085, 8 pages.

U.S. Office Action dated Feb. 23, 2017, issued in U.S. Appl. No. 29/562,755, 8 pages.

U.S. Office Action dated Feb. 27, 2017, issued in U.S. Appl. No. 29/562,756, 7 pages.

U.S. Office Action dated Mar. 17, 2017, issued in U.S. Appl. No. 15/141,152, 14 pages.

International Search Report and Written Opinion dated Aug. 16, 2017, issued in PCT Patent Application No. PCT/US17/29950, 11 pages.

International Search Report and Written Opinion dated Aug. 2, 2017, issued in PCT Patent Application No. PCT/US17/29949, 11 pages.

* cited by examiner

DEVICES, SYSTEMS AND METHODS FOR TREATING MEDICAL DEVICES HAVING PASSAGEWAYS WITH OZONE GAS

TECHNICAL FIELD

The present disclosure generally relates to ozone gas treatment of medical devices and more particularly, is related to devices, systems and methods using agents or gas, such as ozone gas, for cleaning, disinfecting and sterilizing medical devices in a ozone device with multiple cleaning, disinfecting and sterilizing properties, with one or more receptacles, and receiving ports and chambers for ease of cleaning, disinfecting and sterilizing medical devices, medical instruments and medical passageways, such as hoses and/or tubes.

BACKGROUND OF THE DISCLOSURE

Medical devices, medical instruments and medical accessories (collectively "medical devices") require varying degrees of cleaning, disinfection and/or sterilization to prevent bacteria and mold build-up and for safe use and reuse of devices on the same patient and between patients. There are many types of medical devices that have multiple pieces and accessories that require cleaning, disinfection and/or sterilization including, without limitation, hoses, tubes, facemasks, probes, compartments, reservoirs, irrigation systems, pumps and other accessories. Current devices, systems and methods for preparing medical devices for use and/or reuse have proved to be tiring and difficult for users, hospitals and other medical device provider services. Devices often require daily and weekly maintenance steps to prevent bacteria and mold buildup, requiring each part of the device to be cleaned individually, which is difficult and time consuming for users on a daily or weekly basis. Other cleaning methods include soaking the component parts of a medical device in solvents or mixtures for instance of vinegar and water to disinfect the component parts. Because of the inherent nature for many medical devices to collect bacteria and mold, a number of other products are available for consumers to make medical devices safer to use, including but not limited to sprays, UV light devices, cleaning wipes and cleaning brushes.

Ozone gas is powerful and effective for removal of odors, impurities and dangerous pathogens, working by exchanging electron charge with particles that ozone comes into contact with to form oxygen, $O^2$, from the unstable ozone $O3$. This process is particularly useful for purifying air and water and for killing bacteria and microorganisms that the ozone comes into contact with. Ozonators can be used to create ozone from oxygen molecules, often by applying ultraviolet light to the oxygen. Ozone gas is made of oxygen molecules that have been ionized by radiation to form groups of three oxygen atoms, $O^3$, and may be created, for instance in a device, using an ozonator, air, and the application of ultraviolet light to convert oxygen into ozone gas. However, while ozone gas is a powerful cleaning, disinfecting and sterilizing gas, ozone gas must be contained and controlled as it is not safe for users to breath ozone gas until it has safely converted back to oxygen. The amount of time that is needed for ozone to convert safely from ozone to oxygen varies significantly based on the amount of ozone used in a treatment cycle, in some embodiments ranging from 1 minute to 24 hours.

It is a long felt need in the art to provide a device, systems and methods that can treat medical devices and medical device passageways with one device using ozone gas, requiring minimum disassembly and yet part specific treatment, all in one or more connected and closed-loop systems for safe use treatment with ozone gas and ease of use by a user. It is further a need to provide connector units to connect a variety of medical devices and medical device passageways for treatment with ozone gas.

Other systems, methods, apparatus features, and advantages of the present disclosure will be or become apparent to one with skill in the art upon examination of the following drawings and detailed description. It is intended that all such additional systems, methods, apparatus features, and advantages be included within this description, be within the scope of the present disclosure, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

SUMMARY OF THE DISCLOSURE

The present disclosure relates to a device, system and method for cleaning, disinfecting and sterilizing medical devices, the system comprising, a device with an ozone operating system; a distribution line fluidly connected to the ozone operating system for receiving and distributing ozone gas; a first receptacle on the device, wherein the distribution line is fluidly coupled to the first receptacle for releasing ozone gas; a connector unit, wherein the connector unit is configured to be fluidly connected at a proximal end to the first receptacle on the device and fluidly connected at a distal end to a proximal end of a hose in one embodiment, in another embodiment to be fluidly connected to a second receptacle on the device, and in another embodiment to be fluidly connected to the proximal end of a medical device; and an exhaust port configured to be fluidly coupled to the distal end of the hose, such that ozone gas passes through the fluid passageway and is exhausted.

DETAILED DESCRIPTION

Figure 1:
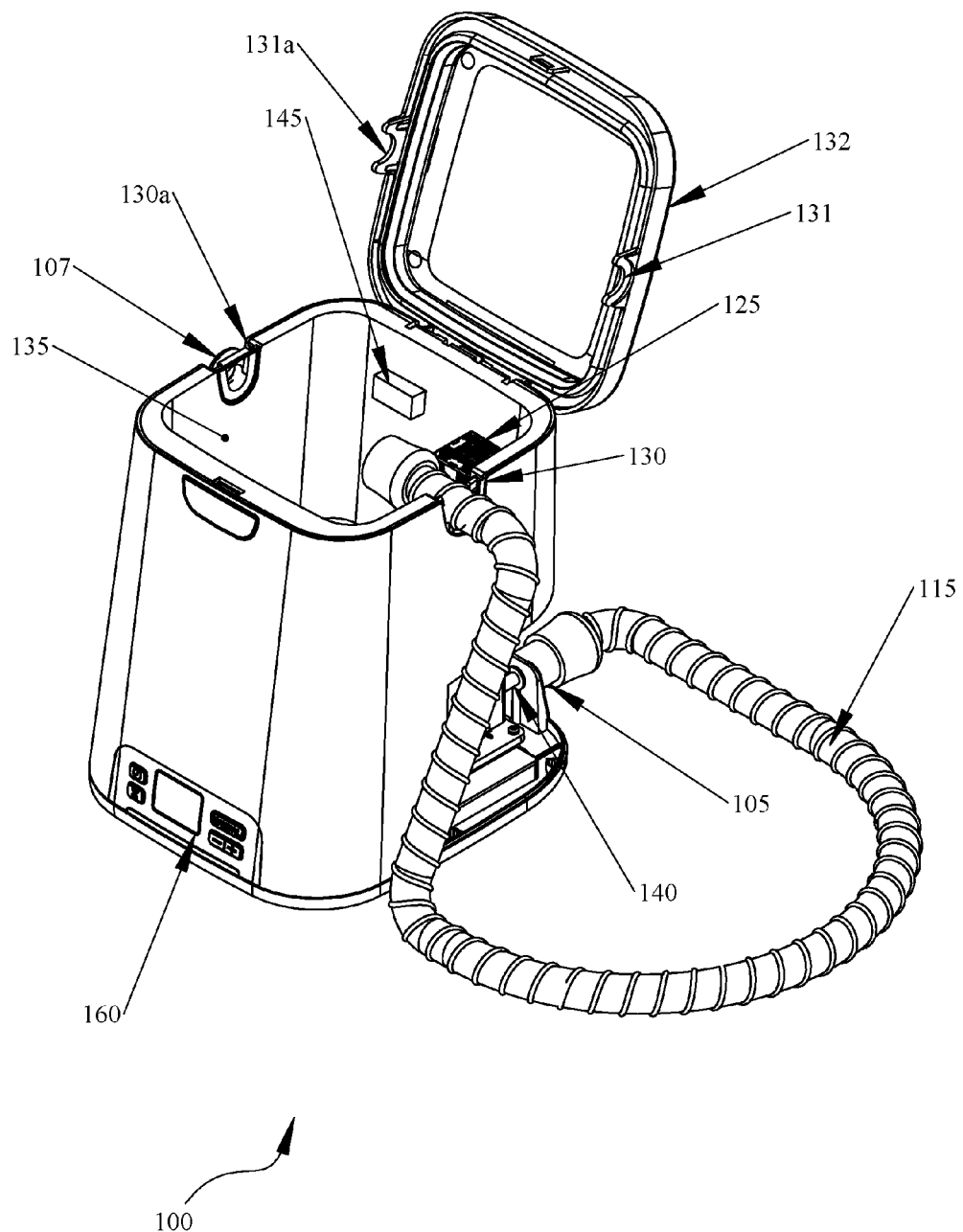
FIG. 1 is a perspective view of an ozone treatment device, in accordance with an embodiment of the present disclosure.

FIG. 1 is a perspective view of an ozone treatment device 100 for treating a medical device tube or hose 115, and medical devices and medical device accessories with ozone.

The medical devices may include any medical devices with passageways including, without limitation, tubes and hoses. As used herein, treating with ozone refers to the use of ozone to clean, disinfect and/or sterilize In accordance with this embodiment, an ozone operating system is embedded at the bottom of the device 100 behind a compartment door for ease of access by a user. The ozone operating system in this embodiment including an air pump, such as an aquarium pump, for pumping air and an ozone generator for receiving the air and creating ozone gas. In this embodiment an ozone distribution line 140 is coupled to the ozone operating system wherein the distribution line 140 releases ozone into a first ozone delivering receptacle 105, as shown in FIG. 1. In accordance with this embodiment, the first receptacle 105 is configured to fluidly couple to a proximal end of a medical device hose 115, such as a continuous positive airway pressure device hose. A second ozone receiving receptacle 130 on the device 100 is designed to engage the distal end of the medical device hose 115, such that when a top lid 132 is in a closed position, tabs 131 engage the second receptacle and form a secure seal surrounding the hose 115. In accordance with this embodiment, the second receptacle is fluidly coupled to a gas-tight compartment 135 with an exhaust port 125 embedded therein. The gas-tight compartment 135 can be used to clean, disinfect, and/or sterilize medical devices and accessories made of materials that do not degrade in the presence of ozone, such as CPAP facemasks, as an example, thereby closing a closed loop ozone process. As such the ozone gas traverses from the ozone operating system, to a distribution line, to a first receptacle, through a hose, through a second receptacle, into a gas-tight sanitization chamber, and to an exhaust port. The exhaust port 125 in accordance with this embodiment is coupled to the gas-tight compartment 135 and exhausts ozone from the fluid passageway described in the present embodiment for reuse and/or release. In accordance with this embodiment, an oxidizing catalyst is coupled to the exhaust port 125 for collecting and breaking down ozone gas into oxygen, for safe release. In accordance with this embodiment, ozone generated in the device 100 is released from the ozone operating system into the first receptacle 105 and ozone gas traverses from the device 100 into the hose 115 and is released through the exhaust port 125.

In accordance with the embodiment shown in FIG. 1, the device further includes a third receptacle, 130a, wherein both the second receptacle 130 and the third receptacle 130a have a removable seal 107. In accordance with this embodiment, the removable seal 107 on the second receptacle 130 and third receptacle 130a allows the medical device hose 115 to be fluidly connected into the second receptacle 130 or third receptacle 130a while maintaining a closed-loop system and preventing release of ozone gas from the closed-loop system prior to conversion of the ozone gas back to oxygen. In accordance with this embodiment and the closed-loop system described, the ozone gas is released into a gas-tight compartment 135 to treat medical devices and accessories placed in the gas-tight compartment 135 in the device 100. In accordance with this embodiment, medical devices and accessories can be placed in the gas-tight compartment and cleaned, disinfected and/or sterilized, while hoses and tubes are cleaned, disinfected and/or sterilized with the ozone gas from the ozone operating system, through the first receptacle and into the hose and exhaust port, in a closed-loop system as described. In accordance with this embodiment, the transfer of ozone gas from the ozone operating system to the second and/or third receptacle 130 and 130a, can be accomplished with one or more hoses, distribution lines or connectors.

In accordance with the embodiment shown in FIG. 1, the ozone treatment device 100 also includes a user interface coupled to the ozone operating system 160, a timer coupled to the ozone operating system, a sensor 145 for sensing remaining ozone gas in the hose 115, gas-tight compartments 135 and/or anywhere in the closed loop system, and a safety switch to prevent start of an ozone process or use of a medical devices during an ozone process and an oxidizing catalyst coupled to the exhaust port 125 to collect and break down ozone.

Figure 1A:
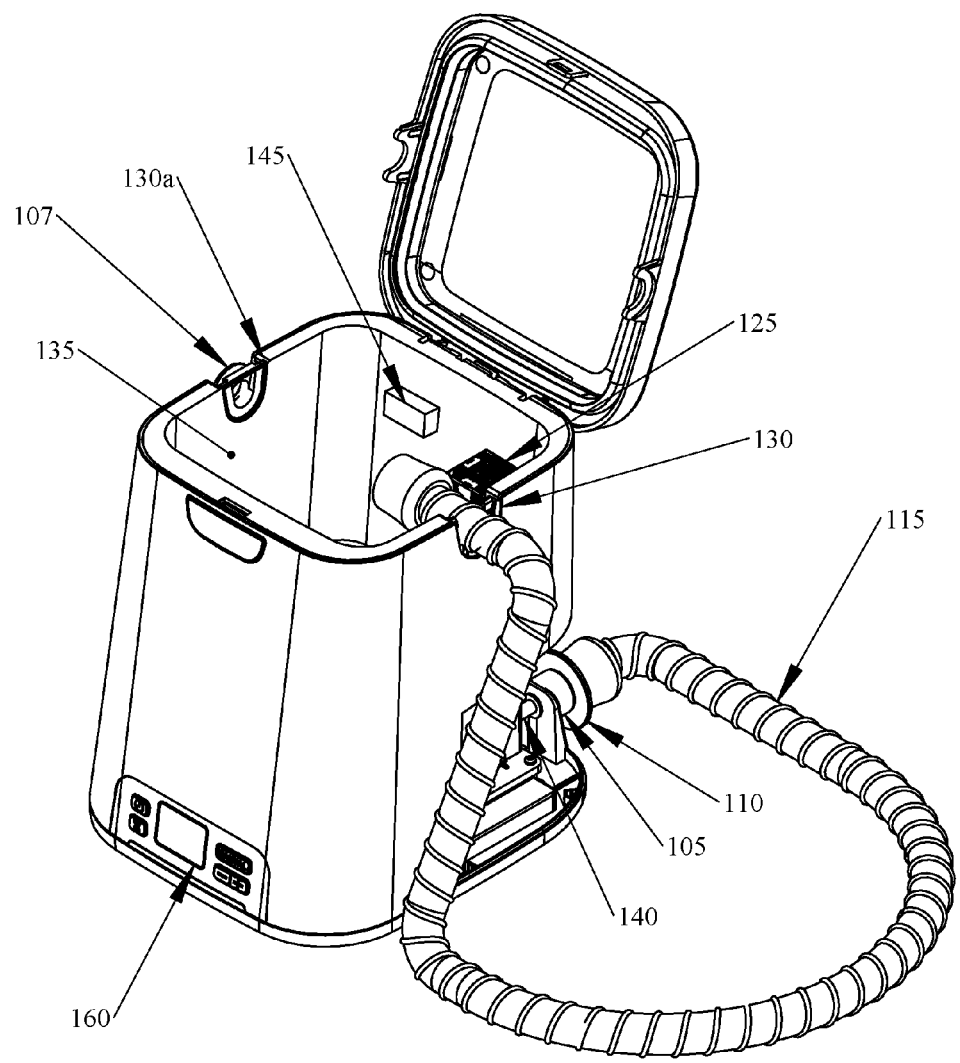
FIG. 1A is a perspective view of an ozone treatment device with a connector unit, in accordance with an embodiment of the present disclosure.

FIG. 1A is a perspective view of an ozone treatment device 100 for cleaning, disinfecting and sterilizing a medical device tube or hose 115, and medical devices and medical device accessories. In accordance with this embodiment, an ozone operating system is embedded in the device 100, the ozone operating system in this embodiment including an air pump, such as an aquarium pump, for pumping air and an ozone generator for receiving the air and creating ozone gas. In this embodiment an ozone distribution line 140 is coupled to the ozone operating system wherein the distribution line 140 releases ozone into a first receptacle 105, as shown in FIG. 1A. In accordance with this embodiment, the first receptacle 105 is configured to be fluidly coupled to a proximal end of a connector unit 110. The connector unit is sized to be fluidly coupled at the distal end of the connector unit to the proximal end to the hose 115. In accordance with this embodiment, the second receptacle 130 on the device 100 is designed to engage the distal end of the hose 115, such that when a top lid 132 is in a closed position, tabs 131, 131a engage the second receptacle and form a secure seal surrounding the hose 115. In accordance with this embodiment the second receptacle 130 is fluidly coupled to an exhaust port 125, in this example, through a gas-tight compartment 135 with the exhaust port 125 embedded in the device 100. The gas-tight compartment 135 can be used to clean, disinfect, and/or sterilize medical devices and accessories made of materials that do not degrade in the presence of ozone, such as CPAP facemasks, as an example, thereby closing a closed loop ozone process. As such, the ozone gas traverses from the ozone operating system, to a distribution line 140, to a first receptacle 105, through a hose 115, through a second receptacle in the hose 115, into a gas-tight compartment 135, and to an exhaust port 125. The exhaust port 125 in accordance with this embodiment is coupled to the to the gas-tight compartment 135 exhausts ozone from the fluid passageway described in the present embodiment for reuse and/or release. In accordance with this embodiment, an oxidizing catalyst is coupled to the exhaust port 125 for collecting and breaking down ozone gas into oxygen, for safe release. In accordance with this embodiment, ozone generated in the device 100 is released from the ozone operating system into the first receptacle 105 and ozone gas traverses from the device 100 into the hose 115 and is released through the exhaust port 125.

In accordance with the embodiment shown in FIG. 1A, the connector unit 110 allows the device 100 to be coupled to any device hose, by providing a first receptacle 105 on the device that fluidly couples to the connector unit 110. For example, in one embodiment the connector unit 110 may be sized to couple at the proximal end to the first receptacle 105 and on the distal end to a CPAP hose 115. In another embodiment, the connector unit 110 may be sized to couple at the proximal end to the hose and at the distal end to an endoscope. Similarly adapters and means to change the distal end of the connector unit 110 to fit a variety of sized tubes for any medical device are disclosed herein.

Figure 2:
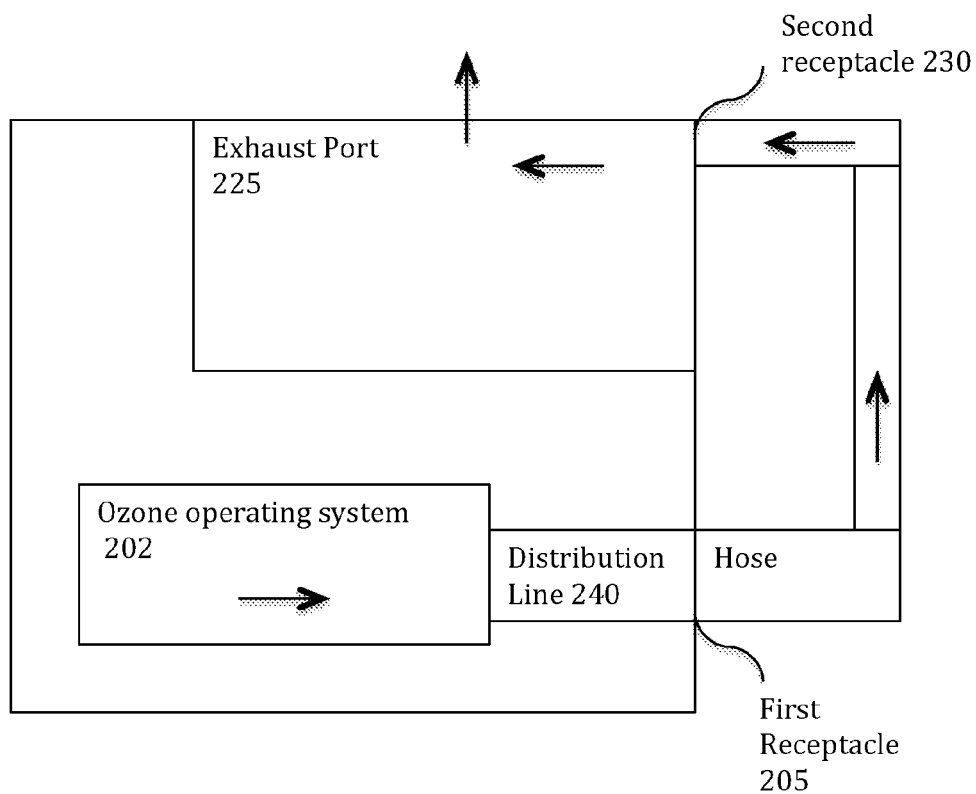
FIG. 2 is a schematic illustration of an ozone process in accordance with an embodiment of the present disclosure.
Figure 2A:
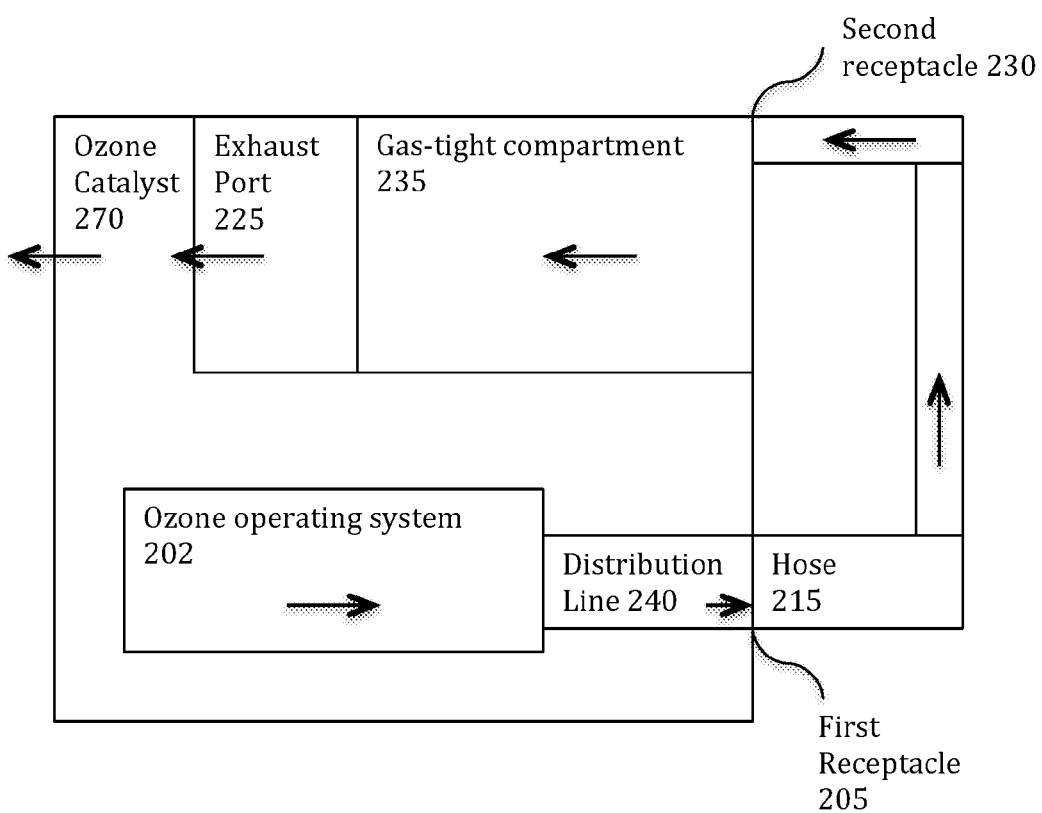
FIG. 2A is a schematic illustration of an ozone process in accordance with an embodiment of the present disclosure.

FIGS. 2 and 2A are schematic sketches showing closed-loop ozone processes in accordance with an embodiment of the present disclosure. In accordance with this embodiment, an ozone treatment system 200 with a reverse loop ozone process is described, wherein the device has a first receptacle 205 and a second receptacle 230 that fluidly couple to a medical device hose 215 for providing a closed loop ozone process in accordance with an embodiment of the present disclosure. In accordance with this embodiment, the ozone treatment system 200 has an ozone operating system 202 including an ozone pump 201 coupled to an ozone generator 203, for producing ozone gas, and a distribution line 240 that carries ozone gas to a first receptacle 205. Ozone gas migrates in this embodiment through the coupled hose 215 and exits the hose into the exhaust port 225, before the ozone gas is release or recycled from the closed-loop system described.

Similar to FIG. 2, FIG. 2A shows an ozone operating system 202 fluidly coupled to a first receptacle 205 with a distribution line 240, with ozone gas migrating into the hose 215 and through the second receptacle 230 on the device 100 into a gas-tight chamber for cleaning, disinfecting and/or sterilizing medical instruments and accessories in the gas tight chamber, before the ozone gas is released or recycles from the closed loop system through an exhaust port 225. In this embodiment an oxide filter 270 is further shown for collecting and breaking down ozone gas into oxygen.

In accordance with the methods disclosed in FIGS. 2 and 2A, a method of treating a medical device with ozone gas is disclosed, the method describing an ozone process of producing ozone gas in a device with an ozone operating system, migrating ozone gas through a distribution line through a first receptacle in the device and into a hose of a medical device, and exhausting ozone gas from the hose of the medical device. In accordance with this method, a second receptacle on the device may be used on the device with an exhaust port and/or a gas-tight compartment coupled to an exhaust port and housed in the device, such that the ozone gas is re-circulated into the device before being removed, released or re-circulated from the system, in a closed-loop ozone process.

Figure 3:
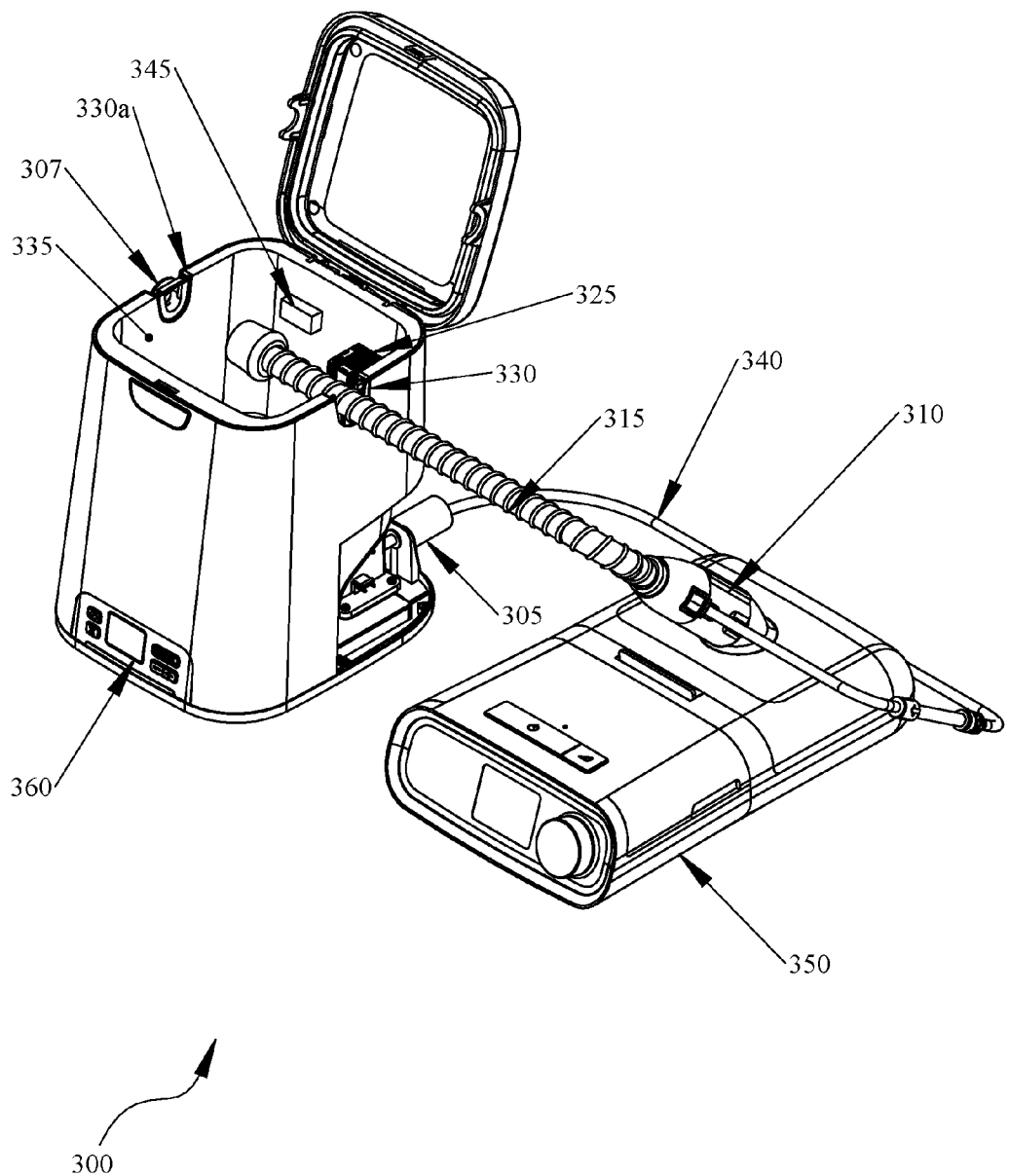
FIG. 3 is a perspective view of an ozone treatment device coupled to a hose and a medical device, in accordance with an embodiment of the present disclosure.

FIG. 3 shows a perspective view of an ozone device with an ozone operating system, in accordance with an embodiment of the present disclosure. In this embodiment, a distribution line 340 traverses a first receptacle 305 and attaches at a distal end to a connector unit 310. In this embodiment the distribution line traverses into the connector unit 310, which is coupled at a proximal end to a medical device 350 and at the distal end to a medical device hose 315, and ozone is released into the hose and/or into a cavity in the medical device 350. In this embodiment a second receptacle 330 and a third receptacle 330a, with a seal 307 are provided such that the hose 315 can be connected as shown through the second receptacle 330 to release ozone gas into a gas-tight compartment 335 and be exhausted through exhaust port 325. In accordance with this embodiment, a sensor 345 is provided in the gas-tight compartment 335 to sense the amount of ozone gas in the closed loop system described herein. In this embodiment the sensor 345 is coupled to the user interface 360 for providing ozone process information to a user, including but not limited to ozone levels remaining in the gas tight compartment 335, ozone cycle time, and ozone safety signals. In accordance with this embodiment, the device 300 and the methods and systems described may further have a user interface 360 coupled to the ozone operating system, a timer coupled to the ozone operating system, a safety switch 365 to prevent start of an ozone process or use of a medical device during an ozone process, and an oxidizing catalyst such as an magnesium oxide filter coupled to the exhaust port 325 to collect and break down ozone.

As such, in accordance with one embodiment of the present disclosure, a system comprising, a device 300 with an ozone operating system; a distribution line 340 fluidly connected to the ozone operating system for receiving and distributing ozone gas; a first receptacle 305 on the device, wherein the distribution line 340 traverses the first receptacle and connects to a connector unit 310; the connector unit 310, wherein the connector unit 310 is configured to be fluidly connected to a medical device 350 and to a medical device hose 315; a second receptacle 330 that engages the hose 315 when the lid 332 is in a closed position with a free end immersed in a gas-tight compartment 335 in the device 300, is described.

Figure 4:
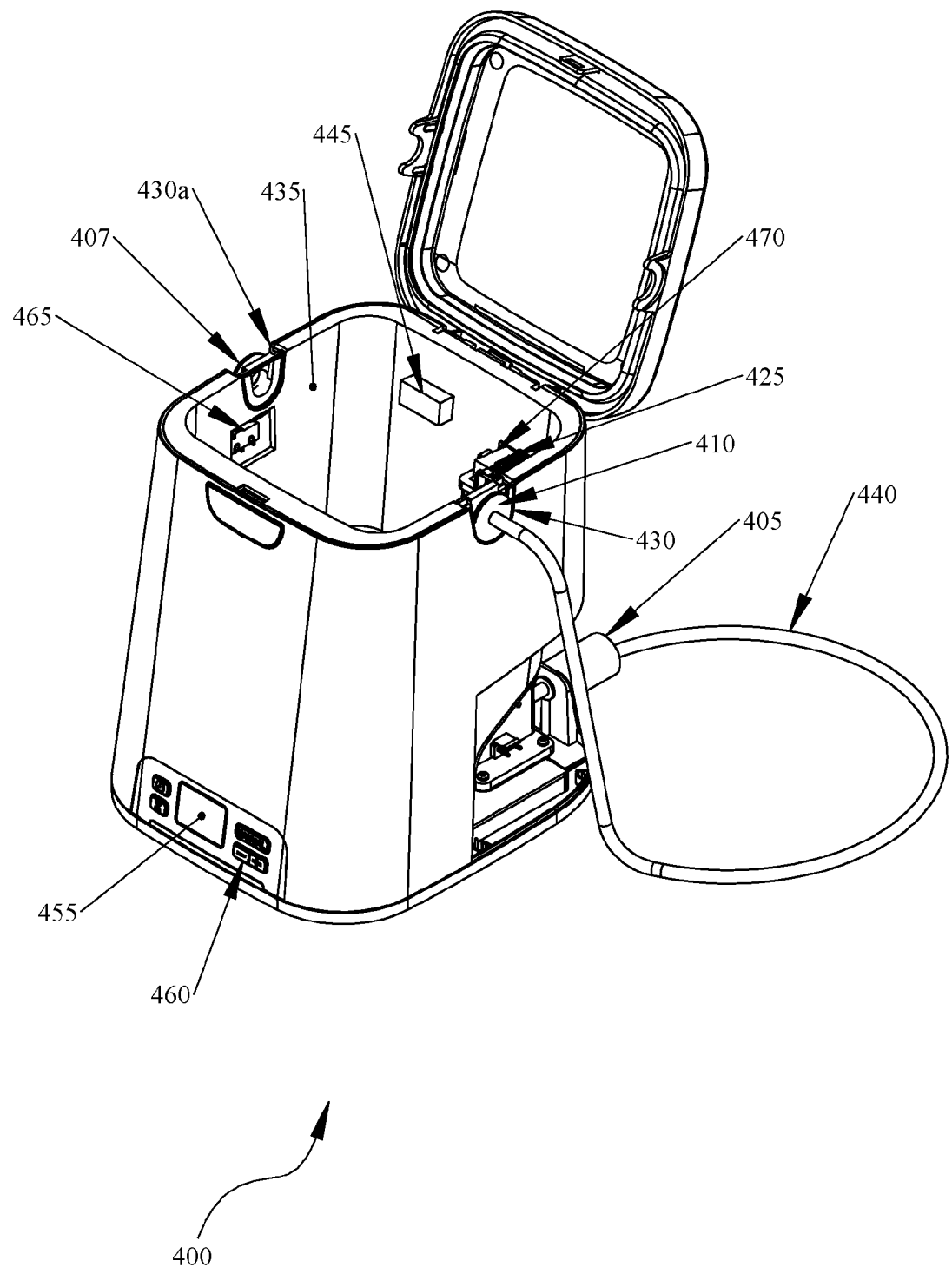
FIG. 4 is a perspective view of an ozone treatment device with an ozone distribution line for recirculating the ozone into the device, in accordance with an embodiment of the present disclosure.

FIG. 4 is a perspective view of a device 400 with an ozone operating system, showing devices, methods and systems for cleaning, disinfecting and sterilizing medical devices and medical device accessories. In accordance with this embodiment, an ozone operating system is embedded in the device 400, the ozone operating system in this embodiment including an air pump, such as an aquarium pump, for pumping air and an ozone generator for receiving the air and creating ozone gas. In this embodiment an ozone distribution line 440 is coupled to the ozone operating system wherein the distribution line 440 traverses a first receptacle 405, as shown in FIG. 4. In accordance with this embodiment, the first receptacle 405 is configured to allow the distribution line 440 to traverse through the first receptacle 405 and engage the second receptacle, which is fluidly coupled to a gas-tight compartment 435 with an exhaust port 425 embedded therein. The gas-tight compartment 435 can be used to clean, disinfect, and/or sterilize medical devices and accessories made of materials that do not degrade in the presence of ozone, such as CPAP facemasks, as an example, thereby closing a closed loop ozone process, whereby ozone gas traverses from the ozone operating system, to a distribution line, through a first receptacle and second receptacle, into a gas-tight chamber, and to an exhaust port. The exhaust port 425 in accordance with this embodiment is coupled to the to the gas-tight compartment 435 and exhausts ozone from the fluid passageway described in the present embodiment for reuse and/or release. In accordance with this embodiment, an oxidizing catalyst is coupled to the exhaust port 425 for collecting and breaking down ozone gas into oxygen, for safe release.

In accordance with yet another embodiment of the present disclosure, a device with an ozone operating system comprising; a first receptacle, wherein the first receptacle is adapted to fluidly transfer ozone gas from the ozone operating system to a hose; and a second receptacle, wherein the second receptacle is adapted to fluidly transfer ozone gas from the hose to an exhaust port, is described. In accordance with this embodiment the device further comprises a gas-tight compartment, wherein the exhaust port is coupled to the gas-tight compartment. The device in the present embodiment further comprises a connector unit, wherein the first end of the connector unit is configured to fluidly couple to the first receptacle and a second end is configured to fluidly couple to a first end of the hose. In accordance with this embodiment second receptacle on the device is configured to engage with a second end of the hose, allowing ozone gas to be released from the hose, through the second receptacle, into the gas-tight compartment. The device in the present embodiment further comprises a user interface coupled to the ozone operating system, a timer coupled to the ozone operating system, a sensor coupled to the ozone operating system for sensing remaining ozone in the medical device, an air pump coupled to the ozone operating system and an oxidizing catalyst coupled to the exhaust port to collect and break down ozone.

In addition to the devices, systems and methods shown in the proceeding examples, the closed-loop systems described include, in some embodiments, steps for delaying the start of an ozone process of a for a fixed period of time from the last ozone process for the safety of the consumers. The step of delaying the start time may range from may range from about 30 seconds to about 24 hours, depending on the device being treated and the level of cleaning, disinfection and/or sterilization required. In addition the step of sensing remaining ozone in a the medical devices being treated further increases the safety of the present treatment systems and methods for users, while also indicating to users that a medical device has been fully treated in accordance with user guidelines and required ozone exposure numbers. As such, the user interface may display a variety of ozone process information to a user, including but not limited to ozone cycle time, device being treated, ozone levels as detected by sensors, level of treatment required based on an assessment of bacterial, mold, dirt or other criteria on a device being treated, light or sound indicators, and consumable product indicators, for the convenience of users.

The present disclosure discloses, devices, systems and methods of using ozone gas in closed-loop systems to clean, disinfect and/or sterilize medical devices, medical device hoses and tubes and accessories. Examples of medical devices that may be cleaned, disinfected and/or sterilized in accordance with the embodiments described in the present disclosure include but are not limited to: surgical instruments, irrigation systems for sterile instruments in sterile tissues, endoscopes and endoscopic biopsy accessories, duodenoscopes, endotracheal tubes, bronchosopes, laryngoscopes blades and other respiratory equipment, esophageal manometry probes, diaphragm fitting rings and gastrointestinal endoscopes, infusion pumps, ventilators, and continuous positive airway pressure devices (CPAP), prone to bacterial build-up because of humidified air and contact with a patients mouth. Many of the devices listed above include passageways that are difficult to clean, disinfect and sterilize, such as any of the endoscopes, probes, ventilators and CPAP devices and related hoses.

The present disclosure thus discloses unique cleaning, disinfecting and sterilizing devices with one or more receptacles and connector units for cleaning, disinfecting and/or sterilizing multiple medical devices, medical tubes and accessories. The devices, systems and methods described may include multiple connector units of different sizes and shapes, multiple ozone distribution lines from a device, wherein the devices may be of any size and shape, a timer, a sensor for sensing ozone in the closed-loop systems, a display for displaying cycle parameters and information, medical device cycle levels, cycle times, a controller for controlling release of ozone into the closed-loop systems, a locking mechanism for locking the device, an exhaust port, and a oxygen catalyst coupled to the exhaust port and uniquely designed connector units that connect to multiple medical devices.

It should be emphasized that the above-described embodiments of the present disclosure, particularly, any "preferred" embodiments, are merely possible examples of implementations, merely set forth for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure and the present disclosure and protected by the following claims.

What is claimed is:

1. An ozone treatment system comprising:
an ozone operating system;
a first receptacle fluidly coupled to the ozone operating system, the first receptacle configured to receive ozone gas from the ozone operating system and to fluidly couple to a proximal end of an ozone conveyance line, said ozone conveyance line further comprising a distal end; and
a gas tight compartment comprising:
a lid and base comprising a plurality of walls, wherein said lid is movable between an open and a closed position, said lid and said plurality of walls define a cavity when said lid is in a closed position; and
a second receptacle configured to receive and engage with an intermediate portion of said ozone conveyance line so as to form a gas tight seal with the distal end of said ozone conveyance line disposed within said cavity, wherein said intermediate portion is between said proximal end and said distal end of said ozone conveyance line;
wherein:
said second receptacle is at least partially defined by at least one of said plurality of walls and said lid; and
said ozone operating system is configured to generate ozone gas for conveyance to said cavity of said gas tight compartment by said ozone conveyance line.

2. The ozone treatment system of claim 1, wherein said second receptacle is at least partially defined by said lid and one of said plurality of walls.

3. The ozone treatment system of claim 1, wherein:
said lid is coupled to said base and is movable between an open and said closed position;
at least one of said plurality of walls comprises both a lid sealing surface and a conveyance line sealing surface; and
said second receptacle is defined at least in part by said conveyance line sealing surface.

4. The ozone treatment system of claim 3, wherein when said lid is in said closed position:
a first portion of said lid engages said lid sealing surface; and
a second portion of said lid defines at least a portion of said second receptacle.

5. The ozone treatment system of claim 4, wherein said second portion of said lid and said lid sealing surface form said gas tight seal with said intermediate portion of said ozone conveyance line.

6. The ozone treatment system of claim 3, wherein:
said lid further comprises a sealing element; and
when said lid is in said closed position:
a first portion of said lid engages said lid sealing surface; and
said sealing element engages at least a portion of said intermediate portion of said ozone conveyance line, such that said second receptacle is at least partially defined by said conveyance line sealing surface and said sealing element.

7. The ozone treatment system of claim 6, wherein said sealing element extends from a downward facing side of said lid when said lid is in said closed position.

8. The ozone treatment system of claim 1, wherein:
said second receptacle defines a passageway into the cavity of said gas tight compartment;
the distal end of said ozone conveyance line is larger than said passageway.

9. The ozone treatment system of claim 1, wherein said ozone conveyance line is a hose of a medical instrument.

10. The ozone treatment system of claim 9, wherein said hose is a hose of a continuous positive airway pressure device.

11. The ozone treatment system of claim 10, further comprising an oxidizing catalyst downstream of said exhaust port, wherein said oxidizing catalyst is configured to break down ozone gas exhausted by said exhaust port.

12. The ozone treatment system of claim 11, wherein said oxidizing catalyst comprises magnesium oxide.

13. The ozone treatment system of claim 9, further comprising a mask coupled to the distal end of said hose.

14. The ozone treatment system of claim 1, further comprising an exhaust port fluidly coupled to said gas tight compartment, wherein the exhaust port is to exhaust ozone gas from said cavity.

15. The ozone treatment system of claim 1, further comprising an ozone sensor within said cavity.

16. The ozone treatment system of claim 1, wherein gas tight compartment is integral with said ozone operating system.

17. The ozone treatment system of claim 1, wherein said ozone operating system and said gas tight compartment are coupled to said base such that a position of the ozone operating system is fixed relative to a position of the gas tight compartment.

18. The ozone treatment system of claim 1, further comprising an air pump fluidly coupled to the ozone operating system.

19. An ozone treatment system comprising:
an ozone operating system configured to fluidly couple to a proximal end of a hose of a medical device, said hose further comprising a distal end; and
a gas tight compartment defined at least in part by a base comprising a plurality of walls and a lid, wherein:
said lid is movable between an open and a closed position; and
said plurality of walls comprises a first wall;
wherein said first wall and said lid are configured to define a receptacle configured to receive and form a gas tight seal with an intermediate portion of said hose, said intermediate portion being between said proximate and distal ends; and
said ozone operating system is configured to generate ozone gas for conveyance to said gas tight compartment by said hose.

20. The ozone treatment system of claim 19, wherein:
said first wall comprises an upward facing surface and a first portion of said receptacle;
said lid defines a second portion of said receptacle; and
when said lid is in said closed position and said intermediate portion is disposed within said receptacle:
a first portion of said lid engages said upward facing surface;
the first and second portions of said receptacle engage said intermediate portion of said hose to form said gas tight seal.

21. The ozone treatment system of claim 20, wherein when said intermediate portion of said hose is disposed within said receptacle, at least part of said intermediate portion is below said second portion of said receptacle.

* * * * *